United States Patent [19]

Pfleger

[11] Patent Number: 5,398,356
[45] Date of Patent: Mar. 21, 1995

[54] X-RAY TABLE

[76] Inventor: Frederick W. Pfleger, 1152 Barbara Dr., Cherry Hill, N.J. 08003

[21] Appl. No.: 82,729

[22] Filed: Jun. 28, 1993

[51] Int. Cl.⁶ ............................................. A61G 7/10
[52] U.S. Cl. ......................................... 5/608; 5/601; 5/611
[58] Field of Search .................... 5/601, 608, 607, 611; 108/147; 248/188.2, 908

[56] References Cited

U.S. PATENT DOCUMENTS

| | | | |
|---|---|---|---|
| 103,546 | 5/1870 | Berger | 108/147 |
| 1,345,760 | 7/1920 | Frye | 5/611 |
| 3,149,229 | 9/1964 | Morel | 5/601 |
| 3,868,103 | 2/1975 | Pegeot et al. | 5/608 |
| 3,900,906 | 8/1975 | Berthelsen | 5/608 |
| 4,006,499 | 2/1977 | Young | 5/608 |
| 4,572,493 | 2/1986 | Hubert | 5/608 |
| 4,761,000 | 8/1988 | Fisher et al. | 5/608 |
| 4,847,929 | 7/1989 | Pupovic | 5/608 |
| 5,083,625 | 1/1992 | Bleicher | 5/611 |
| 5,095,560 | 3/1992 | Volker | 5/611 |
| 5,172,442 | 12/1992 | Bartley et al. | 5/611 |
| 5,197,393 | 3/1993 | Yeakle | 108/147 |
| 5,299,334 | 4/1994 | Gonzalez | 5/611 |

Primary Examiner—Michael J. Milano

[57] ABSTRACT

A table such as an x-ray or operating table with a top positionable into multiple positions and angular orientations with respect to a mounting base such that the positions or orientations include variable elevated positions, variable transverse positions, variable longitudinal positions, variable angular orientations in the longitudinal direction, variable angular orientations in the transverse direction, and variable rotational orientations.

15 Claims, 5 Drawing Sheets

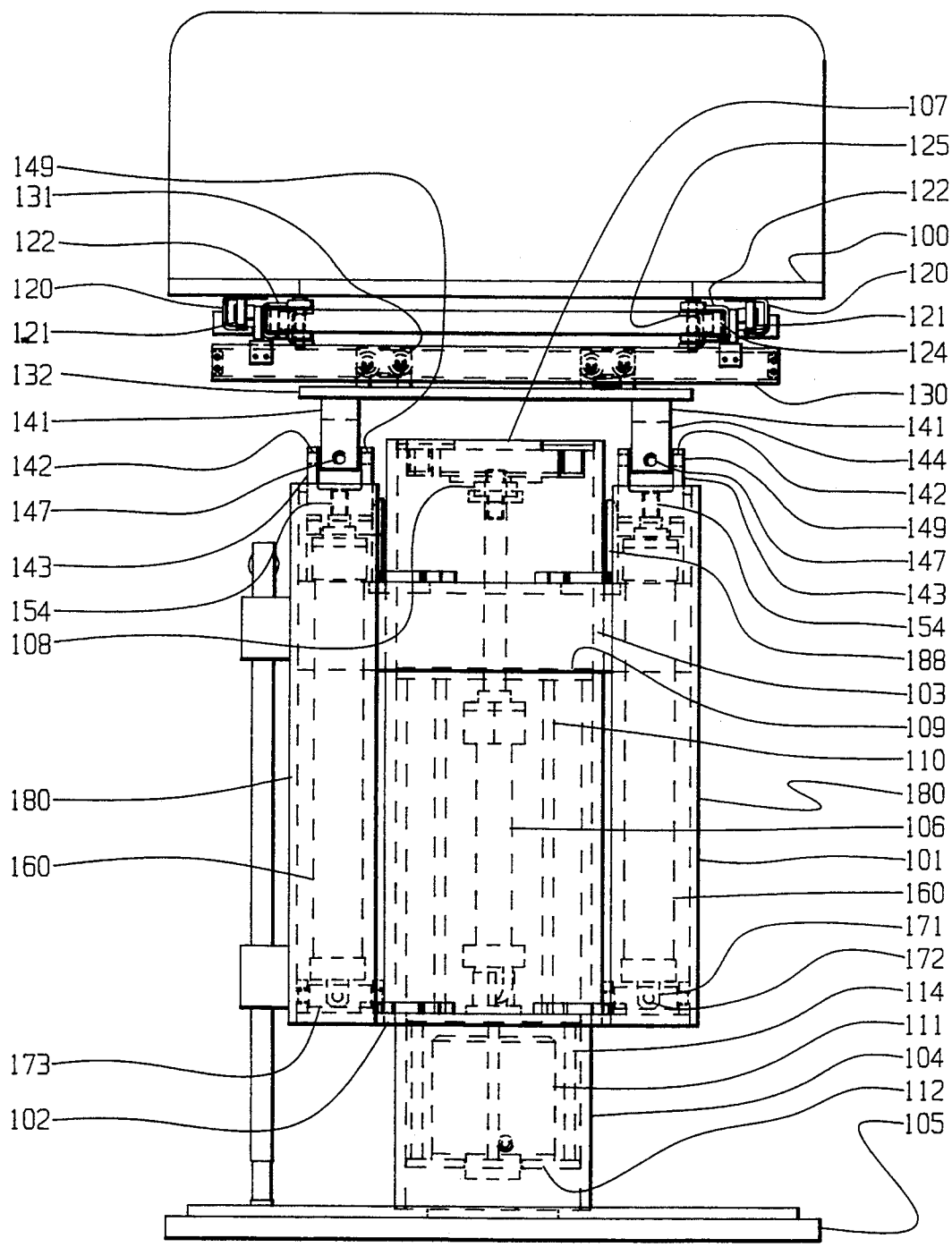
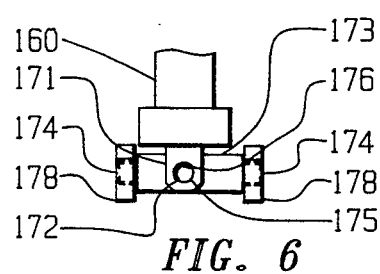
FIG. 3
FIG. 6

X-RAY TABLE

BACKGROUND OF THE INVENTION

Existing x-ray and surgical tables available today are limited in the amount and kind of movement that they can provide to a doctor or a technician. With the continued advancements in procedures used for diagnostic and clinical processes, it is becoming more important that the doctors can position the patient in many positions, both to present the parts of the patient in the most advantageous position for the doctor, and, as in the case of x-ray, to allow the body parts to move into a natural position for any body position. Also, positioning the body parts in various positions allows medicines or diagnostic fluids to flow naturally in the manner the doctors or technicians desire. As an example, if a patient is injected with CO2 gas, gases naturally rise; therefore, if a doctor wishes to have the gas flow into the lower extremities, it is desirable that the lower extremities are positioned in an upward direction. This is also true if it is desired to have the gas flow to the left extremities or the right extremities, the right or left should be elevated. In cases where liquids are injected, it may be useful to have gravity drain the injection from certain areas. As a result, it is desirable to lower the sights from which it is desirable to have the injection flow.

In the existing art, tables exist which raise and lower the table top, cradles exist that are add-ons to existing tables that enable rocking of the body from side to side, and tables exist which provide elevation of the body to an upright position but do not perform in both directions, do not move to 90 degrees from the horizontal or do not allow for the diagnostic equipment to follow the body positions desirable. Since state of the art diagnostic equipment requires free movement both above and below the body as well as to the front or rear of the body, the table top movements must be achievable without affecting the free movement of the diagnostic or clinical procedures equipment.

SUMMARY OF THE INVENTION

Among the objects of this invention is to provide a table surface for a patient whether human or animal in which the table surface can be moved up or down, left or right, back or forth, rotated, and also can lift or lower each end of the table surface to a 90 degree position as well as raise the edge of the table up to provide a forward or rearward tilt to the body.

It is a more particular object of this invention to provide all these motions without the need for additional surfaces to be provided.

It is a more particular object of this invention to provide all of these motions while still enabling diagnostic or other equipment full access above and below the table.

It is a more particular object of this invention to provide all of the above motions with controls easily located and easy to operate.

These and other objects of the invention will become apparent from the following description.

BRIEF DESCRIPTION OF DRAWINGS

FIG. 3 is an end elevation view of the table with the top elevated and located over the center of the base assembly.

FIG. 6 is a partial view of one of the swivel elements.

DESCRIPTION OF PREFERRED EMBODIMENT

Figure 1:
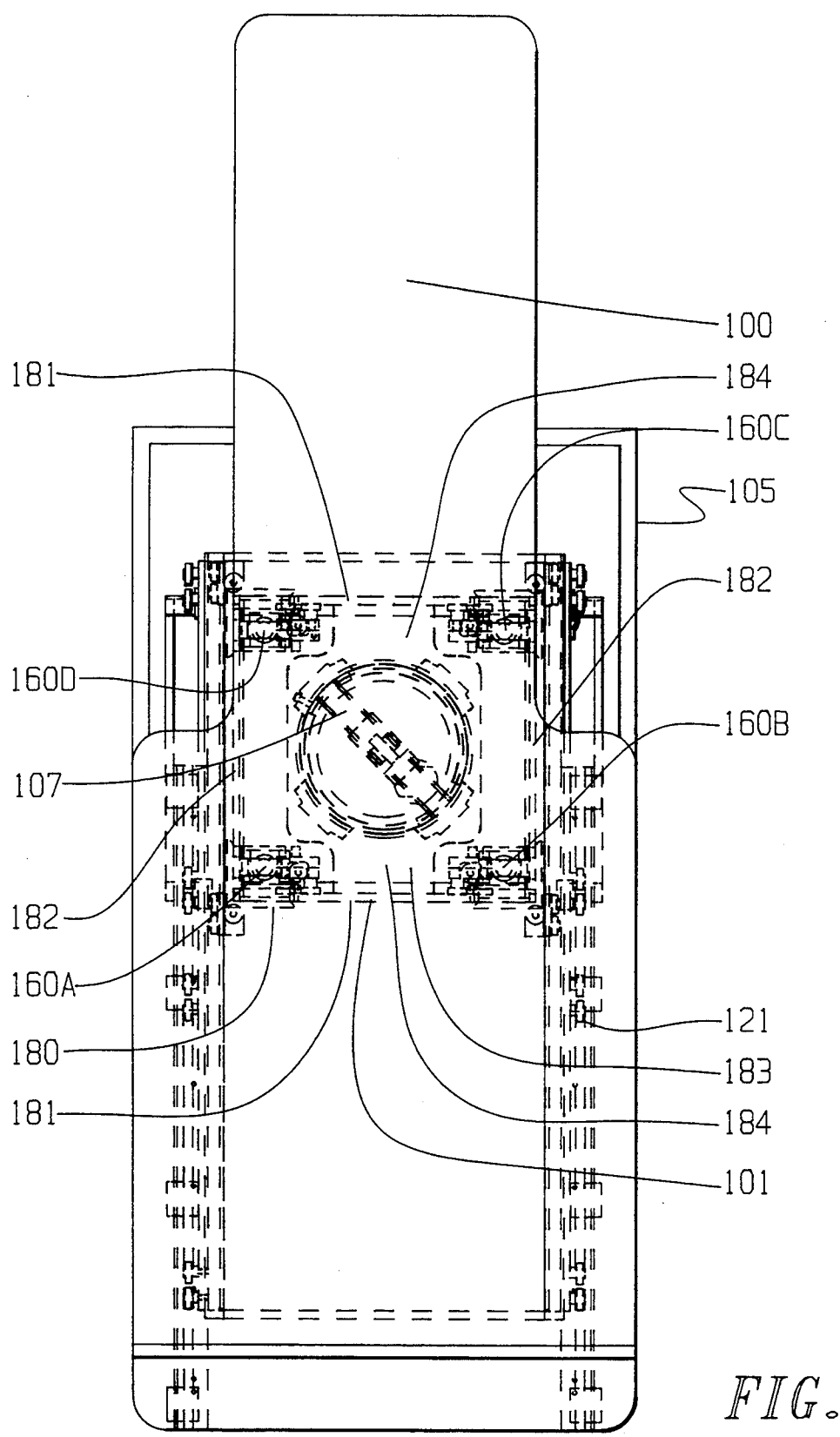
FIG. 1 is a top view showing the table top located over the center of the base assembly.
Figure 2:
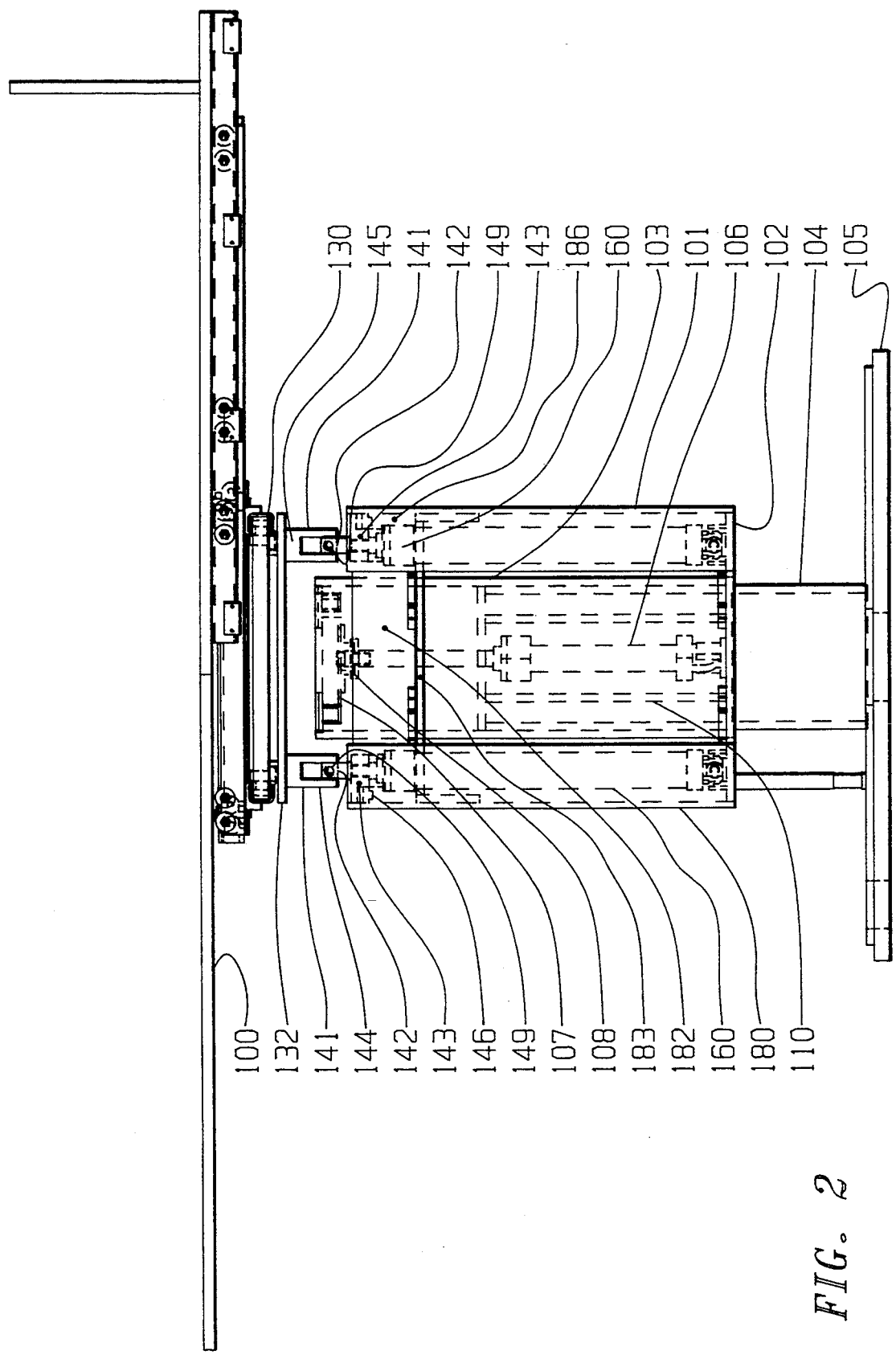
FIG. 2 is a front elevation view of the table top located over the center of the base assembly.

Referring to FIGS. 1,2,& 3 a table surface 100 is mounted to a base unit 101 by means to be described later, which may be attached to the floor by fasteners secured on the lower plate 102 of the base unit 101. It also may be mounted to the floor by means of telescoping concentric tubes 103 & 104. The base of the inner tube 104 can be secured at its lower end to a mounting plate 105 which can be attached to the floor by suitable fasteners. The outer concentric tube 103 can be attached to lower plate 102 of base unit 101 at its lower end while the upper end is attached to the output of a power unit 106 by means of a connecting bar 107. An appropriate thrust bearing 108 and a securing bolt are used in the connection.

Inner concentric tube 104, FIG. 3, has secured at its opposite end from mounting plate 105 a concentric ring 109 which overhangs inwardly to concentric tube 104 a distance sufficient to allow attachment of a plurality of rods 110 to be secured at one end. A power source 111, FIGS. 3 & 4, for power unit 106 is secured to a plate 112 which is secured to the lower rods 114. The fixed end of power unit 106 is secured to the plate 112. The power unit 106 can be an air or hydraulic cylinder, or it can be a screw jack, a rack and pinion or a pulley system. Power can be applied to the power unit 106 by any of the may means available.

Figure 4:
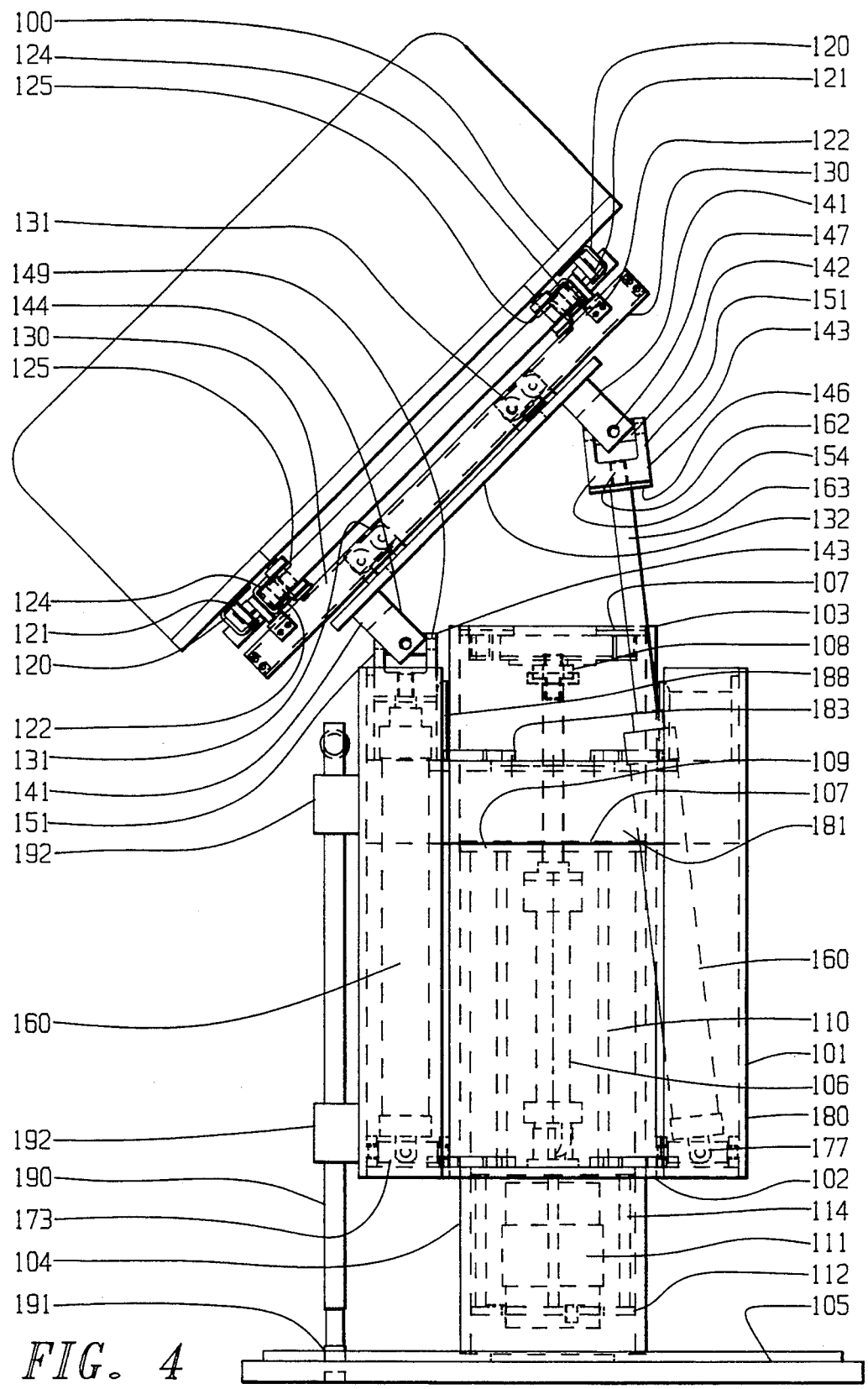
FIG. 4 is an end elevation of the table with the top elevated and tilted in a forward direction.

Activation of power unit 106, therefore, will telescope outer tube 103 on inner tube 104, FIGS. 3 & 4, thus moving lower plate 102 of base unit 101, elevating and lowering it with respect to the floor. Since table surface 100 as previously mentioned is attached to the base unit 101 by means to be described, the table surface 100 will be elevated and lowered with the elevating and lowering of lower plate 102 of base unit 101.

As shown in FIGS. 3 & 4, the table surface 100 is secured to a pair of channel members 120. Channel members 120 are designed to ride on rollers 121 which are mounted on a second pair of channel members 122. This second set of channel members 122 are mounted parallel to channel members 120. Each of the channel members 122 ride on rollers 124 mounted to channel members 125 which are fixed in a given longitudinal position with respect to base unit 101. As a result, when channel members 122 move on rollers 124, the table surface 100 can move the same longitudinal distance as channels 122. Since channel members 120 can move on rollers 121 mounted to channel members 122, the table surface 100 can move an additional longitudinal distance. The total movement is limited by the length of the channel members and the spacing of the rollers.

If the table surface 100 is rectangular in shape, the channels 120 & 122 and the roller sets 121 & 124 can be symmetrical in the longitudinal direction, FIG. 2, about the centerline of the base unit 101. As a result, the table surface 100 can move equal amounts in both longitudinal directions. As shown in FIG. 1, the table surface 100 is of a special shape; therefore limiting the amount of movement in the one direction.

Channel members 125 are secured perpendicular to a pair of channel members 130, FIG. 3. Channel members 130 ride on two (2) sets of rollers 131 which are mounted to an intermediate plate 132. As a result, table surface 100 can move a transverse distance perpendicular to the longitudinal direction, a distance controlled by the length of the channels 130 and the position of the roller sets 131. Therefore, the table surface 100 can move in both a longitudinal direction as well as a transverse direction.

In this particular description, intermediate plate 132 is a square plate, but the configuration is not critical.

Referring now to FIGS. 2, 3 & 4, fastened at each corner of intermediate plate 132 is the output member 141 of a universal swiveling assembly. This universal swiveling assembly is made up of output member 141, swivel member 142 and input member 143. Output member 141 comprises two downward extending legs 144, FIGS. 2 & 5, and a cross member 145. Cross member 145 is fastened to intermediate plate 132. Legs 144 are positioned to fit over swivel member 142 so that it can rotate a total of 90 degrees in both directions. In order to accomplish this rotation, the legs are provided with holes through which a pivot pin 147, FIGS. 3 & 4, can pass. Pivot pin 147 also passes through a hole located on the centerline of swivel member 142. As a result, the legs 144 of output member 141 pivot on the pivot pin 147 a distance of plus or minus 90 degrees. Swivel member 142 is provided at each end with studs 149 which fit into a hole in each of the legs 151 of input member 143. In order for output member 141 to rotate plus or minus 90 degrees as previously stated, the width between the legs 151, which is slightly greater than the width of the swivel member 142, is greater than the width of the legs 144. The centerline of the swivel member 142 and the studs 149 are located from the base 154 of input member 143, a distance greater than the total distance of the diagonal dimension of swivel member 142 plus the thickness of legs 144. As a result, the universal swivel assembly is capable of rotating its output member plus or minus 90 degrees in either direction with respect to the base 154. The base 154 of each universal swivel assembly is secured to the output of a power member 160, in this particular disclosure, a threaded hole 161 mated to a threaded end 162 of a piston rod 163 of a hydraulic cylinder. The power members 160 can be hydraulic cylinders, air cylinders, or they can be screws, racks and pinions or a cable system, depending on the particular application. The other end of each power member 160 is fastened to the output member 177 of a second universal assembly. This other end of power member 160 as shown in FIGS. 3 & 6, is provided with a pair of downward extending legs 171 with bearing holes 172. This second universal assembly is provided with a swivel member 173 with a stud 174 on each end and a cross hole 175 perpendicular to the centerline of studs 174. A pin 176 fits into cross hole 175 and into the bearing holes 172, thus securing power members 160 to this second universal assembly. Studs 174 of swivel member 173 fit into a pair of holes in base member 178 which is secured to lower plate 102.

In this particular application, the power members 160 are located in the four corners of lower plate 102 with the base member 178 secured to each corner of lower plate 102.

Figure 5:
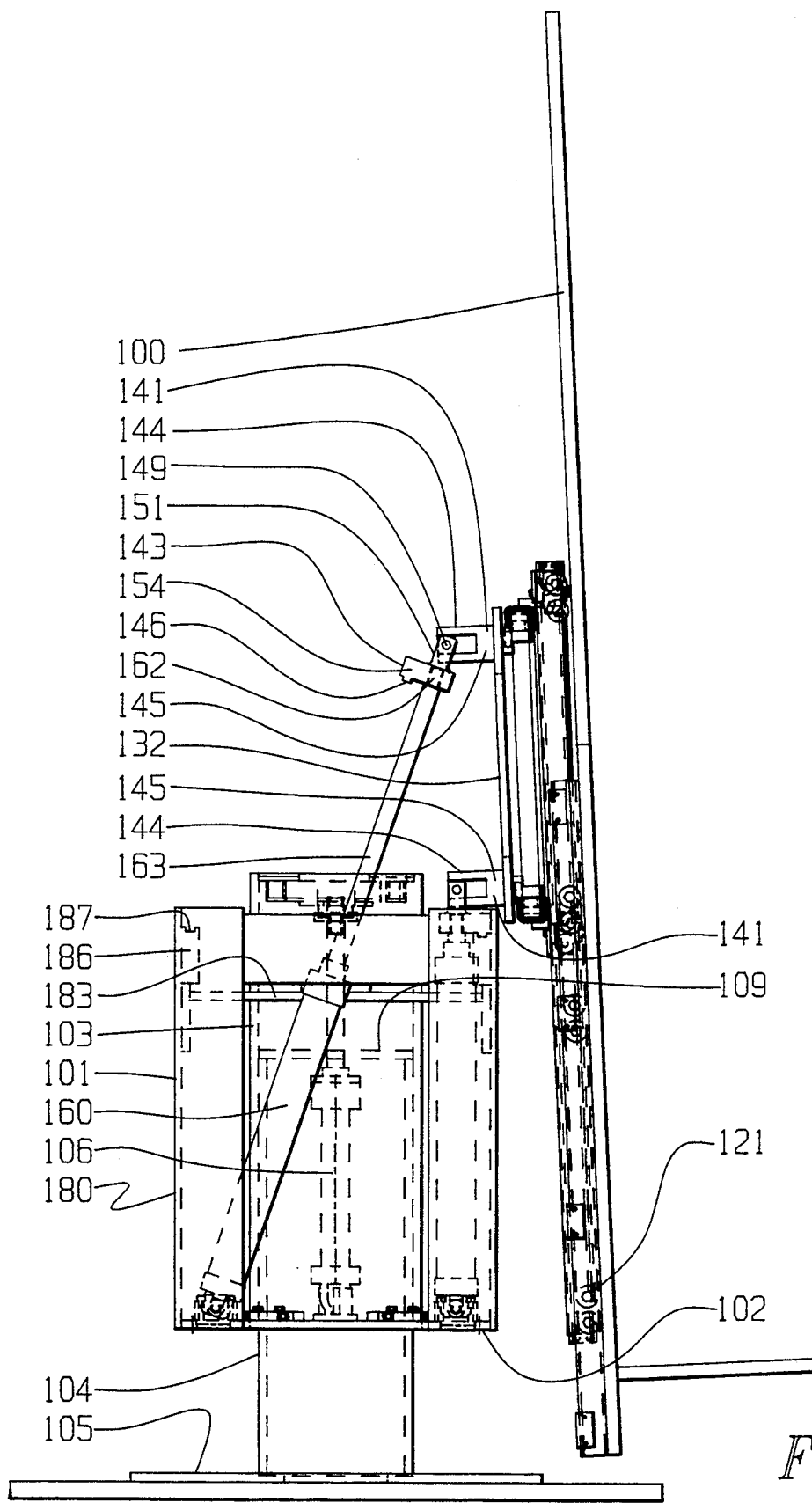
FIG. 5 is an end elevation of the table with the top elevated and tilted to the right so that it is almost perpendicular to the floor.

As shown in FIGS. 4 & 5, the power members 160 are rocked from the normal position, shown in FIGS. 2 & 3, to an angular position with respect to base unit 101 and table surface 100. As a result, the universal assemblies provide the attaching means between power members 160, the intermediate plate 132 to which the table surface 100 is fastened and the lower plate 102 of base unit 101. Although the table surface 100 in FIGS. 4 & 5, is being rocked approximately 45 degrees and 90 degrees, it is obvious that if the power units are stopped anywhere between the positions shown in FIGS. 2 & 3 and FIGS. 4 & 5, the table surface 100 will assume an angle related to the amount of movement of the rod 163.

Ascending from each corner of lower plate 102 is a structural corner angle 180. Near the upper end of each angle 180 are tie bars 181 & 182, FIG. 1. Surrounding outer tube 103 is an upper plate 183 which is fastened to tie bars 181. As a result, angles 180, tie bars 181 & 182, upper plate 183 and lower plate 102 form a box structure around outer tube 103 with lower plate 102 being the base member of the box structure. Since upper plate 183 is only attached to tie bars 181 power members 160 can rotate to the position needed to achieve a full 90degrees of rotation of table surface 100 with respect to base unit 101 in the longitudinal direction. Since the rotation of the table surface 100 does not normally require a full 90 degrees of rotation in the transverse direction (direction perpendicular to the longitudinal direction), the power members 160 do not have to rotate as great a distance. As a result, upper plate 183 is provided with extending arms 184 which are secured to bars 181. Secured in this manner, upper plate 183 acts to stabilize the upper end of the box structure. It is obvious that the box structure can be stabilized by other means if greater rotational movement in the transverse direction of table surface 100 is required.

Secured to the upper portion of each corner angle 180 is a seating plate 186, FIG. 2 & 5. As previously mentioned, input member 143 of the first universal joint is fastened to the piston rod 163. In order to stabilize and hold the upper end of power members 160 in position, each input member 143 is provided with an extended portion 146 which mates with a configuration formed in seating plate 186. In this particular disclosure, the configuration is a keyway parallel to the long dimension of seating plate 186 with a stop plate 188, FIG. 3 located at the end of keyway. The extended portion is therefore a key formed on input member 143 which fits into keyway 187. As a result, when downward force is provided by power members 160, input member 143 is held securely in position with respect to seating plate 186.

In the normal position, that is, when all power members 160 are in their non-activated position and providing forces in the downward direction, all input members 143 to universal swivel assemblies 140 are held in a fixed position. Since output members 141 of universal swivel assemblies 140 are secured to intermediate plate 132, the output member 141 cannot pivot. Since the input members 143 and the output members 141 are prevented from rotating when the power members 160 are in the normal position, the universal swivel joint assemblies are rigid. As a result, the table surface 100 is held in a non-rotated position with respect to base unit 100.

If any two adjacent power members are activated, the output piston rods 163 move into an extended position. When a pair of adjacent piston rods 163 elevate, the intermediate plate 132 is moved upward in a direction controlled by which two adjacent power members 160 are operated. Since the portion of intermediate plate 132 above the two power members 160 that are not being operated is held by the output members 141 of the respective universal swivel assemblies, the path of intermediate plate 132 is an arcurate path with the swivel member 142 of the nonactive universal swivel assemblies acts as the centerline of rotation.

As shown in FIG. 1, if adjacent power members 160A & 160B are powered, the table surface 100 will tilt to the left, pivoting on swivel members 142 of the swivel assemblies connected to power members 160C & 160D. If adjacent power members 160C & 160D are powered, the table surface 100 will tilt to the right, FIG. 5, pivoting on swivel member 142 of the swivel assemblies connected to power members 160A & 160B. If adjacent power members 160B & 160C are powered, the table surface 100 will tilt forward, FIG. 4, pivoting on swivel member 142 of the swivel assemblies connected to power members 160D & 160A. If adjacent power members 160A & 160D, FIG. 1 are powered, the table surface 100 will tilt rearward, pivoting on swivel members 142 of the swivel assemblies connected to power members 160C & 160B.

When the base unit is made up of an inner tube 103 and an outer tube 104 concentric with each other as previously described, the two (2) tubes can telescope to provide up and down movement of the table surface 100 with respect to the mounting plate 105. In order to prevent rotation of the two telescoping tubes which will allow rotation of the top surface 100 with respect to mounting plate 105 any appropriate anti-rotational lock unit known in the art can be provided such as the rod 190, FIG. 4, fastened to the box structure by bracket 192 fitting in one of a plurality of holes 191 in mounting plate 105.

What has been described then is a table surface that can be elevated, can be rotated, can be tilted to the left or the right, can be tilted forward or rearward and can be shifted to the left or to the right and forward or rearward, all motions of the table surface occurring while maintaining the base in a fixed position.

What is claimed is:

1. A table comprising a top,
a lower plate,
a four corner mounting for mounting said top to said lower plate,
an actuator for each corner of said four corner mounting having a fixed member and a moveable member,
a universal assembly for each actuator connecting said lower plate to said fixed member of said actuator, a universal swivel assembly for each actuator having an input member connected to said moveable element and an output member connected to one of said four corner mountings,
a home position for each moveable member,
a plurality of variable movements for each moveable member,
such that when the moveable members of any two adjacent actuators are held in said home position and the moveable members of the other two adjacent actuators are moved equally, said four corner mounting assumes unique angular positions with respect to said lower plate.

2. A table according to claim 1 wherein said four corner mounting is a rectangular configuration.

3. A table according to claim 1 wherein said four corner mounting is a square configuration.

4. A table according to claim 1 including a top plate for mounting said top, said lower plate having a given mounting pattern,
such that the mountings on said lower plate are in vertical alignment with said four corner mounting of said top plate.

5. A table according to claim 4 including slides between said top plate and said top,
such that top can be positioned in various positions with respect to said top plate.

6. A table according to claim 4 including a mounting plate,
a column fastened to said mounting plate,
a moveable column fastened to said lower plate slideably and rotatably mounted to said column,
a moveable column actuator between said moveable column and said mounting plate,
such that activation of said moveable column actuator raises and lowers said top plate while said top plate is angulated or rotated with respect to said mounting plate.

7. A table according to claim 1 wherein said output member of said universal swivel assembly is pivotly connected to said input member,
such that said output member can rotate to plus or minus 90 degrees with respect to said input member to allow for plus or minus 90 degrees of movement of said top.

8. A table according to claim 1 wherein said output member can rotate to plus or minus 90 degrees in two perpendicular planes with respect to said input member to allow for plus or minus 90 degrees of movement of said top.

9. A table comprising a top,
a top plate for mounting said top including four mounting points in a rectangular pattern,
a lower plate with four mounting positions in vertical alignment with said four mounting points on said top plate,
an actuator for each of said four mounting points, each having a fixed member and a moveable member,
a universal assembly connected to a fixed member of each actuator and to one of said four mounting positions on said lower plate,
a universal swivel assembly having an input member connected to one of said moveable elements and an output member connected to one of said four mounting points of said top plate,
a home position for each moveable member,
variable extended positions for each moveable member of said actuators,
such that the moveable members of any two adjacent actuators are in home position and the moveable members of the remaining two adjacent actuators are in extended positions causing said top to assume unique positions with respect to said lower plate.

10. A table according to claim 9 including a cross rail assembly, a longitudinal rail assembly, bearings mounted for said rails,
such that the top can move in cross direction with respect to said lower plate and in longitudinal direction with respect to said lower plate while still assuming angular positions with respect to said lower plate.

11. A table according to claim 9 wherein said rectangular pattern is a square.

12. A table according to claim 9 including a mounting plate,
adjustable means connecting said mounting plate to said lower plate,
such that said lower plate can be positioned at various elevations with respect to said mounting plate.

13. A table comprising a top,
an intermediate plate for mounting said top,
a mounting plate,
a column fastened to said mounting plate,
a hollow tube surrounding said column,
a lower plate secured to said hollow tube, four actuators having a fixed member and a moveable member located outside the periphery of said hollow tube and in a rectangular array,
a universal assembly fastening said fixed member of said actuators to said lower plate,
a universal swivel assembly having an output member secured to said intermediate plate and an input member secured to the moveable member of said actuator,
said output member capable of plus or minus 90 degrees of movement in two planes relating to said input member,
such that said top can assume various angular positions to plus or minus 90 degrees with respect to said intermediate plate when any moveable member of two adjacent actuators are in home position and the two moveable members of the other two adjacent actuators are moved an equal amount.

14. A table according to claim 13 including a lift actuator having a moveable member connected to said hollow tube and a fixed member connected to said column,
such that said table can assume various elevated positions and assume various angular positions with respect to said mounting plate.

15. A table according to claim 14 including a rotational joint connecting said moveable member of said left actuator to said hollow tube,
such that said top can assume various rotational positions with respect to said mounting plate while assuming various angular positions with respect to said mounting plate.

* * * * *